(12) United States Patent
Valen

(10) Patent No.: US 8,221,119 B1
(45) Date of Patent: Jul. 17, 2012

(54) DENTAL IMPLANT AND METHOD OF INSTALLING THE SAME

(76) Inventor: Maurice Valen, Holliswood, NY (US)

( * ) Notice: Subject to any disclaimer, the term of this patent is extended or adjusted under 35 U.S.C. 154(b) by 367 days.

(21) Appl. No.: 11/973,502

(22) Filed: Oct. 9, 2007

(51) Int. Cl.
*A61C 8/00* (2006.01)
(52) U.S. Cl. .......................................... 433/174; 606/315
(58) Field of Classification Search .................. 433/173, 433/174; 606/309, 315
See application file for complete search history.

(56) References Cited

U.S. PATENT DOCUMENTS

| | | | | |
|---|---|---|---|---|
| 422,307 | A * | 2/1890 | Libbey | 411/412 |
| 4,103,422 | A | 8/1978 | Weiss | |
| 5,639,237 | A | 6/1997 | Fontenot | |
| 6,129,730 | A * | 10/2000 | Bono et al. | 606/291 |
| 6,371,709 | B1 * | 4/2002 | Papafotiou et al. | 411/412 |
| 6,743,233 | B1 | 6/2004 | Baldwin | |
| 7,273,373 | B2 * | 9/2007 | Horiuchi | 433/174 |
| 7,806,693 | B2 * | 10/2010 | Hurson | 433/174 |
| 7,935,138 | B1 * | 5/2011 | Richelsoph | 606/313 |
| 2001/0055744 | A1 | 12/2001 | Ura | |
| 2004/0121289 | A1 | 6/2004 | Miller | |
| 2004/0153154 | A1 * | 8/2004 | Dinkelacker | 623/16.11 |
| 2005/0147942 | A1 * | 7/2005 | Hall | 433/173 |
| 2006/0204930 | A1 | 9/2006 | Sul | |
| 2008/0014556 | A1 * | 1/2008 | Neumeyer | 433/174 |

FOREIGN PATENT DOCUMENTS

| | | | |
|---|---|---|---|
| EP | 1440669 A1 | * | 7/2004 |
| FR | 2610512 | * | 2/1987 |
| WO | WO 2004/098442 | * | 11/2004 |

OTHER PUBLICATIONS

U.S. Appl. No. 10/668,805, Maurice Valen

* cited by examiner

*Primary Examiner* — Ralph Lewis
(74) *Attorney, Agent, or Firm* — Maxine L. Barasch, Esq.; Keohane & D'Alessandro PLLC

(57) ABSTRACT

A dental implant having a unique thread configuration, which increases the total load bearing area to maximize support values of a successful implant for the same osteotomy when compared to other implant designs. At least one course of helical threads surrounds an elongated, cylindrical body. In an embodiment chosen for the purposes of disclosure, the threads have relatively broad crestal surfaces, typically having a rounded profile. One or more helical secondary threaded grooves are disposed in the crestal surface of the threads. The helical grooves facilitate collection of bone and promote immediate stabilization and osseointegration of the implant. The broad crestal thread design compresses bone in one direction while bone is being collected by the helical grooves in the opposite direction. The result is that the implant is immediately stable in a patient's jaw. The method of installing the dental implant is also novel.

12 Claims, 7 Drawing Sheets

DENTAL IMPLANT AND METHOD OF INSTALLING THE SAME

RELATED APPLICATIONS

The present application is related to my copending application Ser. No. 10/668,805, filed Sep. 24, 2003, which is included herein in its entirety by reference.

FIELD OF THE INVENTION

The invention relates to dental implants, and more particularly, to a screw-type dental implant having helical threads along a shaft. The threads have a broad crest and have at least one helical groove or channel disposed in the crest.

BACKGROUND OF THE INVENTION

The science of dental implantology has been evolving for many years. For an implant to be successful, there must be equilibrium between the implant and the underlying bone when under pressure from chewing. The muscular force from chewing is exerted through the implant design into the underlying bone structure. An inadequate implant design, for example, an implant with poor implant geometry or insufficient implant support values, generates higher stresses against bone, and the implant generally fails because of fibrous tissue build-up and encapsulation over time. To be successful, the implant must directly stimulate the underlying bone to promote equilibrium and osseointegration. Dentists, doctors, and scientists continually strive to develop implants that provide reliable, long-term service to patients into whom such implants are inserted.

Osseointegration is the process by which the bone moves toward the prosthetic implant, developing a close proximity therebetween. Ideally, the bone and implant osseointegrate such that the implant becomes secure in the bone (i.e., the implant has become a "part" of the jawbone).

Osseointegration can be encouraged by stimulating the underlying bone during chewing. This may be accomplished by choosing an appropriate implant geometry, having an adequate Total Surface Area (TSA), and most importantly, sufficient Load Bearing Area (LBA) to reduce stresses and maintain implant stability on a long term basis.

Conversely, bone is naturally stimulated by a tooth root from the downward force resulting from cyclic chewing. This movement stretches the Sharpey's fibers attached to the bone through a pulling action, which causes tension in the bone for osseous stimulation.

A titanium prosthetic dental implant cannot emulate the natural "pulling-type" stimulation described above. Instead, bone stimulation must be achieved through the process of osteocompression on the bone by the implant. Maximizing the LBA of the implant will maximize such compression. The horizontal LBA on any implant is the primary mechanism for bone stimulation and support by the action of osteocompression (metal-to-bone support in a compressive mode). The areas of an implant's surface capable of providing sufficient bone support and physiologic stimulation are the horizontal compressive planes, rather than the vertical implant interface under shear force. If the implant lacks sufficient horizontal load bearing areas, then the implant may act like a knife in the bone (i.e., blade implants), thereby generating greater stresses, and causing the implant to fail.

The laws of physics, particularly Newton's Third Law, dictate that mechanical forces always come in pairs—an applied force and a resisting force, equal in magnitude, opposite in direction, and collinear to establish equilibrium. Therefore, there will always be a force by the implant on the bone, and a resisting force by the existing bone on the implant. The forces resulting from the implant and trabecular bone on one another should be in equilibrium for the implant to be successful. To achieve equilibrium in the bone, successful implant diagnosis and selection should consider the value of the masticatory force magnitude generated through the implant design; the horizontal load bearing values of the selected implant; and the density of bone values or level of mineralization in a specific bone region of the jaw.

The mechanical relationship between implant and bone can be described in units of the modulus of elasticity. The modulus of trabecular bone is 1.5 million psi and cortical bone is up to 3 million psi. On the other hand, titanium is very strong or stiff in comparison, having a modulus of elasticity of 15 million psi. Due to this mismatch, the weaker member is always the bone under compressive or shear forces.

Most conventional prior art implant designs do not provide for large amount of horizontal areas for interfacing with the bone. Prior art implants also have small thread pitches. It would, therefore, be desirable to have a dental implant wherein the load bearing areas are increased through more extensive horizontal planes on the threads of the implant. It would also be advantageous to have a dental implant wherein the threads are spaced apart in accordance with the strength or weakness (i.e., the density) of the bone in which it is to be implanted.

DISCUSSION OF THE RELATED ART

U.S. Pat. No. 4,103,422 for THREADED SELF-TAPPING ENDODONTIC STABILIZER, issued Aug. 1, 1978 to Charles M. Weiss et al., discloses a threaded, self-tapping endodontic stabilizer for insertion in a tooth root canal and into the jawbone of a patient's mouth through a threading aperture in a loose tooth. The WEISS stabilizer includes threads disposed along a longitudinal axis of the stabilizer. The threads have a shallow recess extending along the peripheral edge thereof.

U.S. Pat. No. 5,639,237 For DENTAL PROSTHESIS HAVING INDENTATIONS, issued Jun. 17, 1997 to Mark G. Fontenot, shows a dental implant with a prosthetic attachment having a bulbous proximal end and a threaded distal end having a plurality of convex and concave ridges.

Published United States Patent Application No. 2001/0055744 for DENTAL IMPLANT AND METHOD FOR INSTALLING THE SAME, published Dec. 27, 2001 upon application by Robert S. Ura, shows a dental implant wherein two successive helical threads having two different diameters are disposed along a shaft. The threads have a small pitch and sharp knife-like members.

U.S. Pat. No. 6,743,233 for MEDICAL SCREW AND METHODS OF INSTALLATION, issued Jun. 1, 2004 to Jeffrey P. Baldwin et al., discloses another screw for medical and orthopedic applications, wherein successive sharp, flat threads have different diameters.

United States Published Patent Application No. 2004/0121289 for DENTAL IMPLANT, published Jun. 24, 2004 upon application by Robert G. Miller, teaches a dental implant, wherein the threaded portion carries non-symmetrical threads.

United States Published Patent Application No. 2006/0204930 for HELICAL IMPLANT, published Sep. 14, 2006 upon application by Young-Tack Sul, shows a dental implant having a single course of helical, serrated threads. The threads have a narrow crest and approximately sixty-degree slope.

None of the patents and published patent applications, taken singly, or in any combination are seen to teach or suggest the novel dental implant of the present invention.

SUMMARY OF THE INVENTION

In accordance with the present invention, there is provided a dental implant having a unique thread configuration that maximizes support values of a successful implant for the same osteotomy when compared to other designs. At least one course of helical threads surrounds an elongated, cylindrical body. In an embodiment chosen for purposes of disclosure, the threads have relatively broad crestal surfaces, typically having a rounded profile. One or more helical secondary threaded grooves are disposed in the crestal surface of the threads.

When the implant is installed, the broad crestal thread design compresses bone in one direction while bone is collected by the grooves in the opposite direction. The result is that the implant is immediately stable in a patient's jawbone.

It is, therefore, an object of the invention to provide a dental implant having one or more courses of helical threads.

It is another object of the invention to provide a dental implant, wherein the threads have a broad crest.

It is an additional object of the invention to provide a dental implant, wherein the thread crest carries one or more helical grooves.

It is a further object of the invention to provide a dental implant, wherein the threads are knuckle threads.

It is an additional object of the invention to provide a dental implant having threads of a substantially sinusoidal cross-section and having secondary grooves.

It is a still further object of the invention to provide a dental implant that is adapted to receive a dental restoration directly thereupon.

It is another object of the invention to provide a dental implant that may receive and support various and interchangeable prosthetic abutments for various prosthetic demands.

It is yet another object of the invention to provide a dental implant designed to receive an abutment for a fixed dental bridge.

It is a further object of the invention to provide a dental implant conducive to implantation and installation during a single session or single dental office visit.

It is another object of the invention to provide a method of installing an implant such that a portion of an abutment, whether attached or integral with the implant, sits below the crest of a patient's jawbone.

It is a further object of the invention to provide a method of installing an implant such that an abutment, whether attached or integral with the implant, sits above the crest of a patient's jawbone.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 4b is a pictorial, perspective, and cross-sectional view of the abutment of FIG. 4a.

DETAILED DESCRIPTION OF THE PREFERRED EMBODIMENT

The present invention provides an improved dental implant featuring a unique thread configuration. One or more helical grooves are provided at the crest of the implant's threads. Such a groove and crest arrangement is advantageous and results in superior performance of the implant. The novel implant's thread design results in immediate stabilization of the implant in the bone. In addition, the novel groove and crest configuration stimulates bone formation through osteocompression by the process of electro-streaming potential. The concept of electro-streaming potential is believed to be well known to those of skill in the art.

Figure 1:
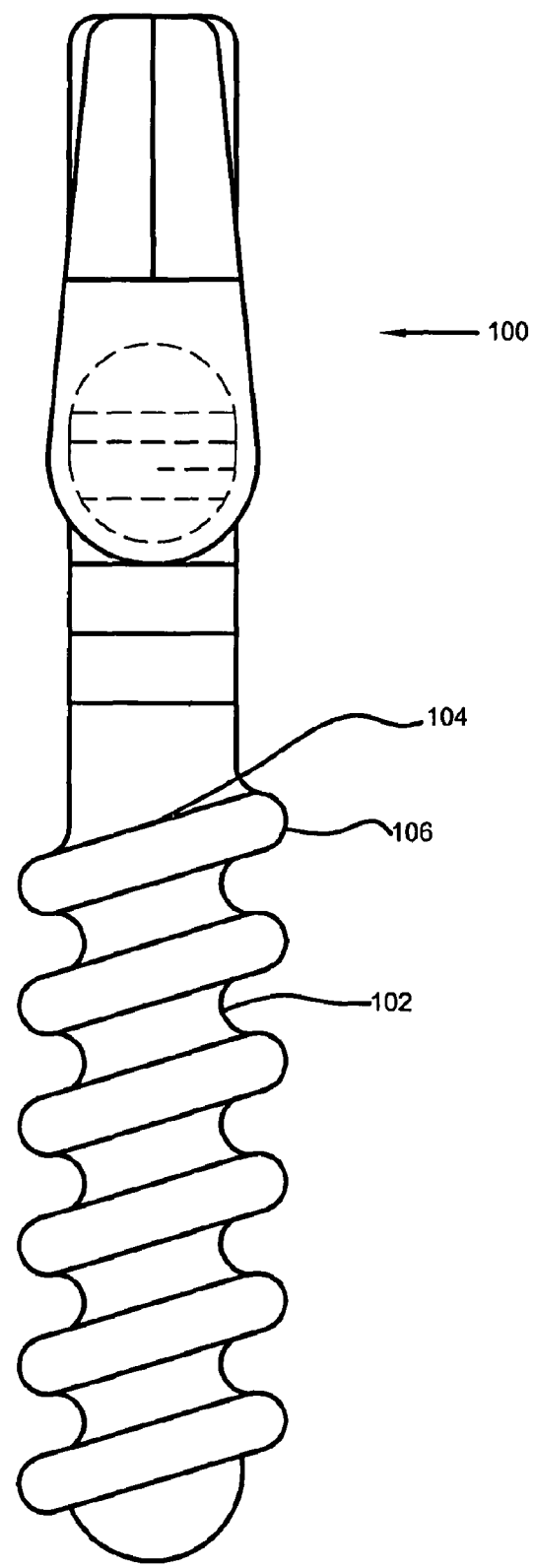
FIG. 1 is a pictorial, perspective view of a dental implant of the prior art with an attached abutment.

Referring first to FIG. 1, there is shown a perspective, pictorial view of a two-piece dental implant of the prior art, without its respective abutment, generally at reference number 100. Implant 100 is of a type well known to those of skill in the art, typically having a single course of threads 104 disposed around an elongated, cylindrical shaft 102.

Threads 104 have a crestal surface 106 disposed at an outer periphery of the thread. Such threads are similar to "knuckle" threads known to those of skill in the fastener arts. Threads 104 may have various profiles including but not limited to a sharp V, a rounded U, or a flat outer surface (i.e., the well-known square or "Acme" threads), depending upon the specific application for which implant 100 is intended. The common feature of threads disposed on dental implants of the prior art is that the threads are typically V-shaped (i.e., have an extremely narrow crest), and typically have a slope in the range of approximately 30 to 60 degrees.

Dental practitioners should choose implants having greater vertical distances between the implant threads (i.e., pitch) where bone is poorly mineralized to accommodate a larger volume of bone under compression between the thread areas. Studies have demonstrated that an implant is best secured in the bone by increasing the LBA (load bearing area) of the implant. Increased LBA allows the compression caused by chewing to be spread over a larger surface area. Such thread space will offset the differences in modulus of elasticity between metal and bone, thereby increasing the implant-to-bone bulk support values in horizontal planes, or the increase of bulk modulus of the weaker member.

Figure 2A:
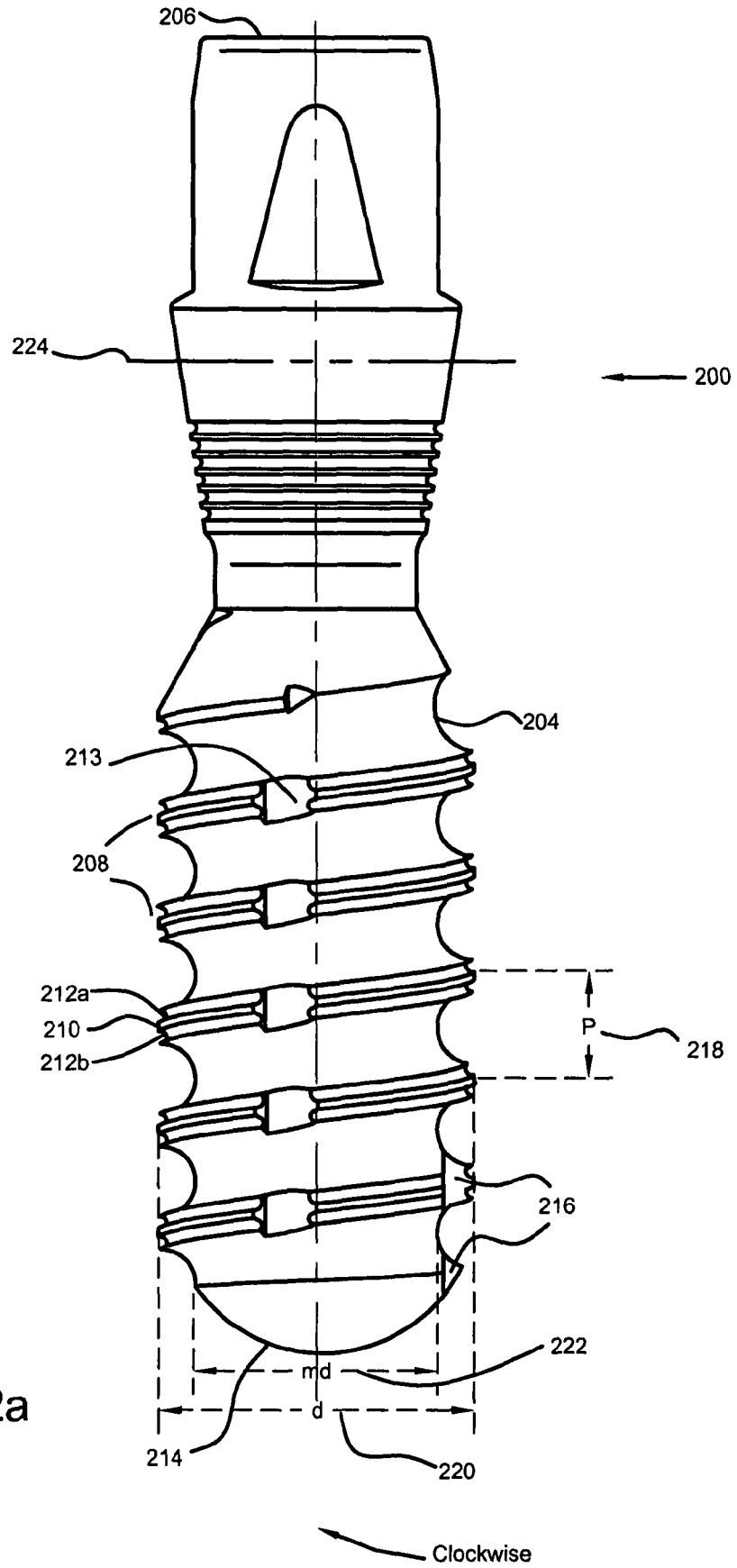
FIGS. 2a and 2b are pictorial, perspective and side cross-sectional views, respectively, of the dental implant in accordance with the present invention.
Figure 2B:
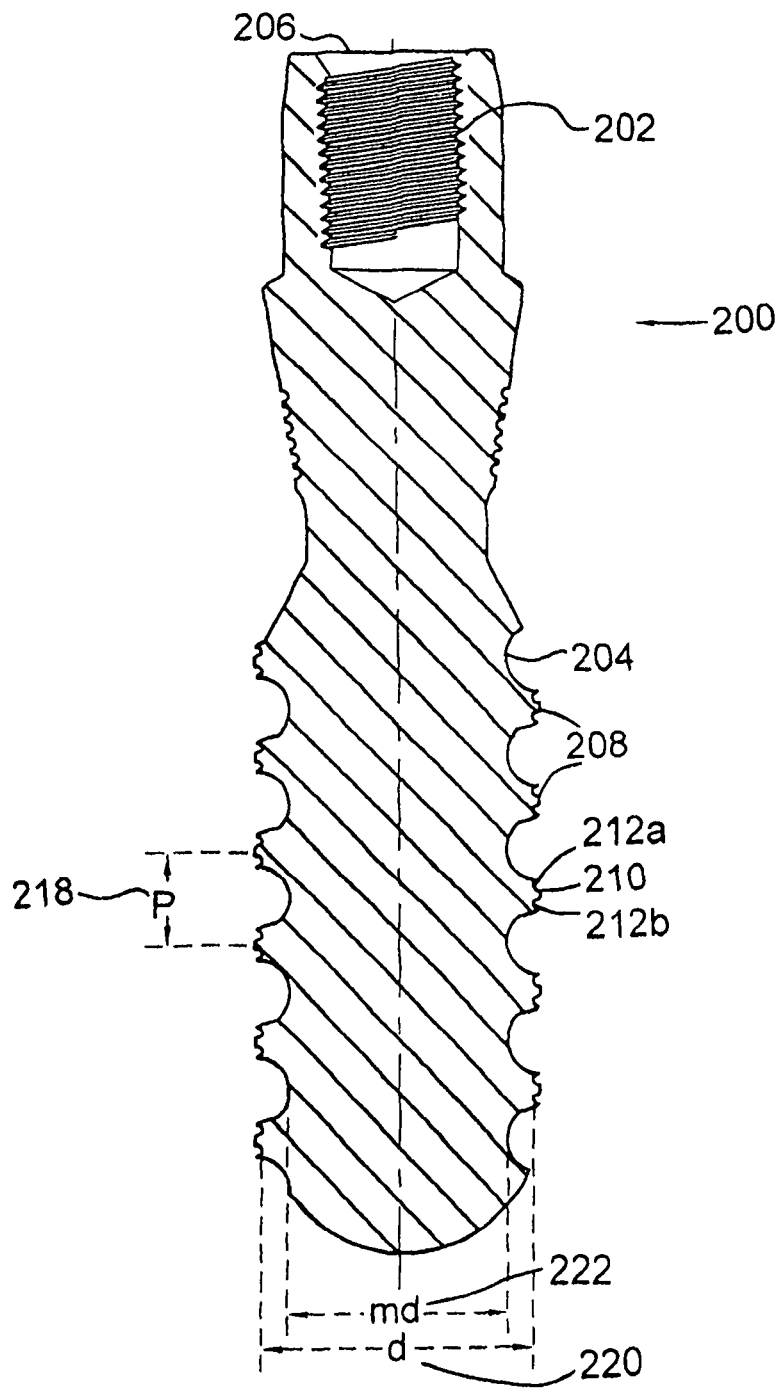

Referring now to FIGS. 2a and 2b, there are shown perspective and cross-sectional views, respectively, of a first embodiment of a dental implant in accordance with the present invention, generally at reference number 200. Implant 200 is a one-piece implant (abutment integral with implant) having internal threads 202 to accept a dental restoration or prosthesis, not shown, as is well known to those of skill in the dental implant arts. Such implants are known as one-piece implants as no intermediary abutment is required between the implant and the prosthesis.

Figure 2C:
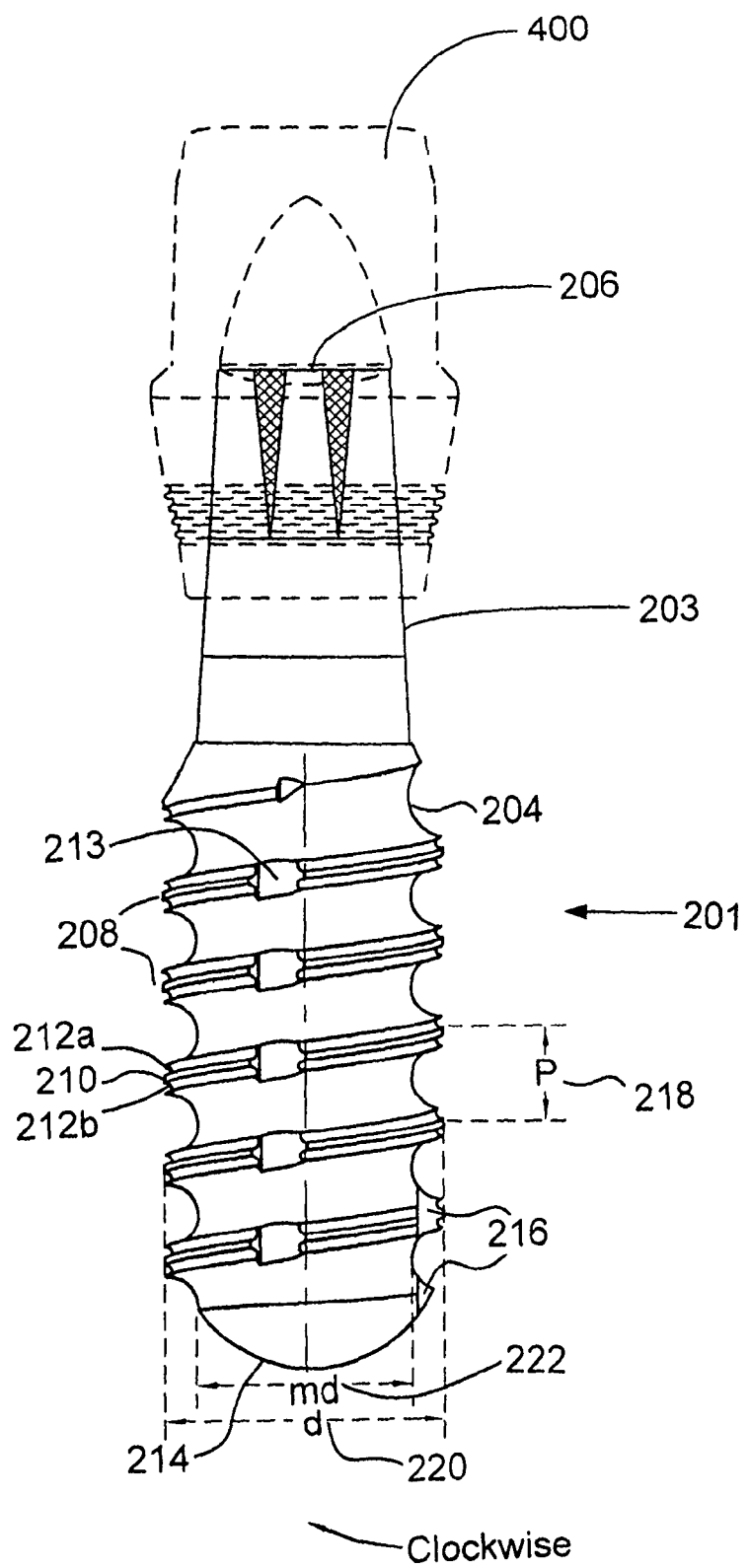
FIG. 2c is a pictorial, perspective view of the dental implant in accordance with the present invention having a Morse taper for receiving an abutment.
Figure 3:
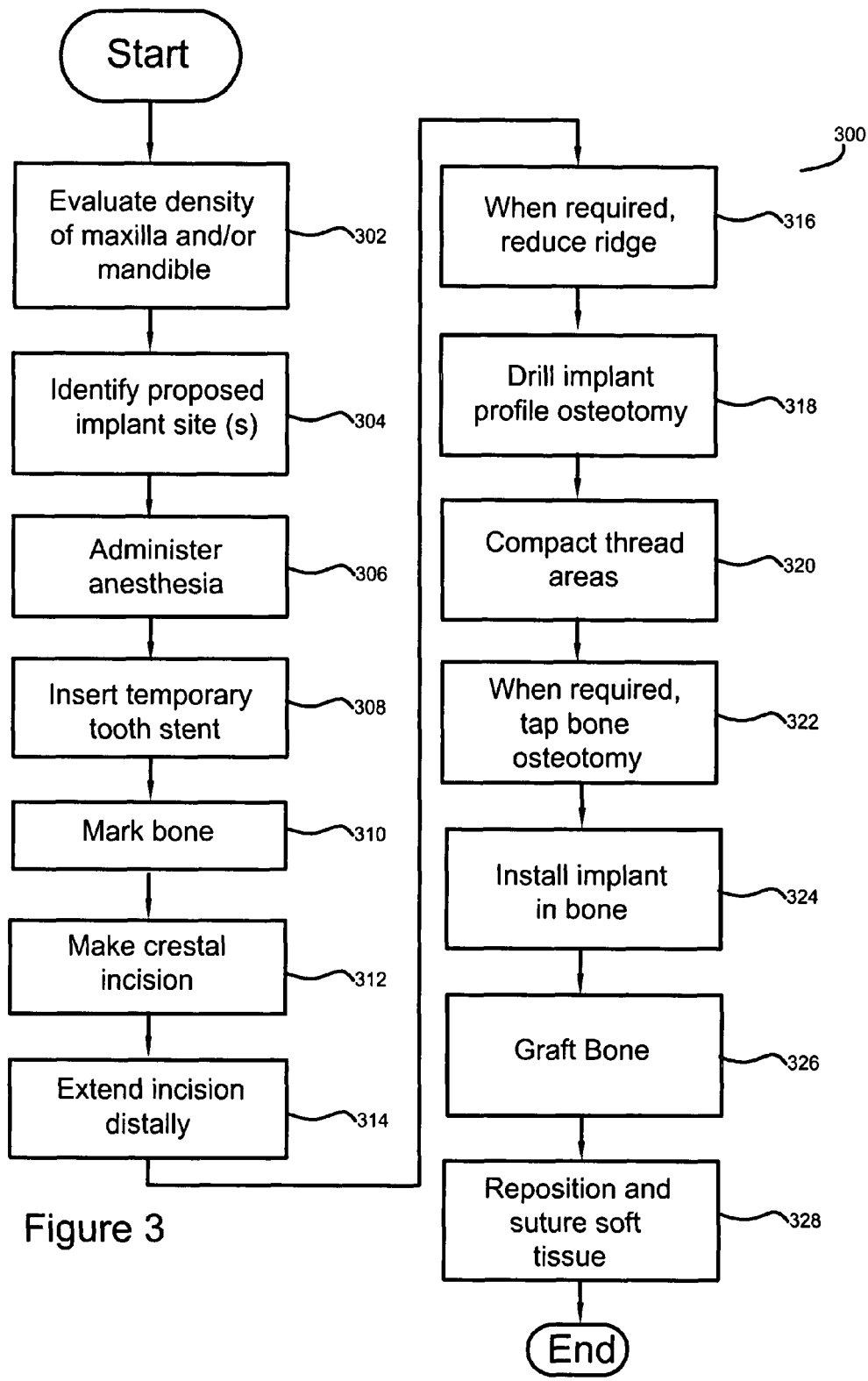
FIG. 3 is a flowchart illustrating the steps for installing the inventive implant.
Figure 4A:
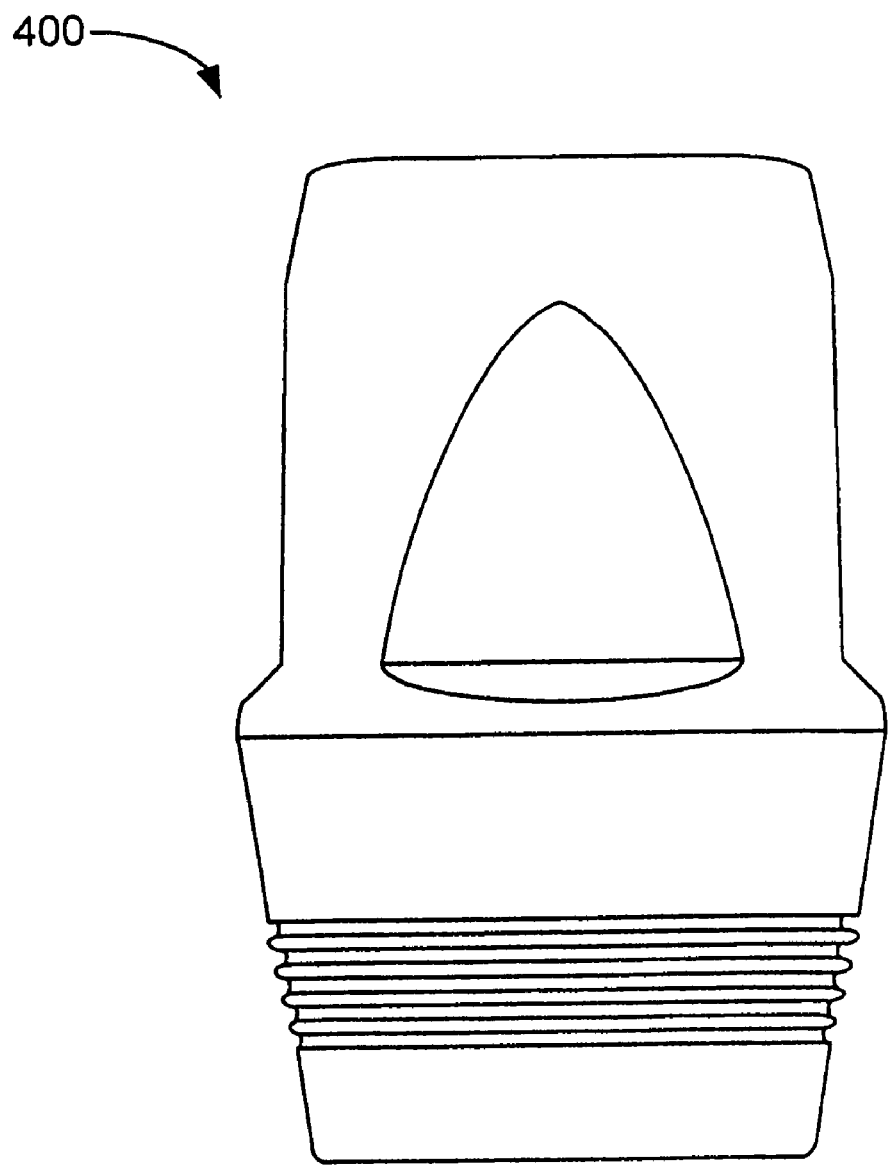
FIG. 4a is a pictorial perspective view of an exemplary abutment attachable to the dental implant of FIG. 2c.
Figure 4B:
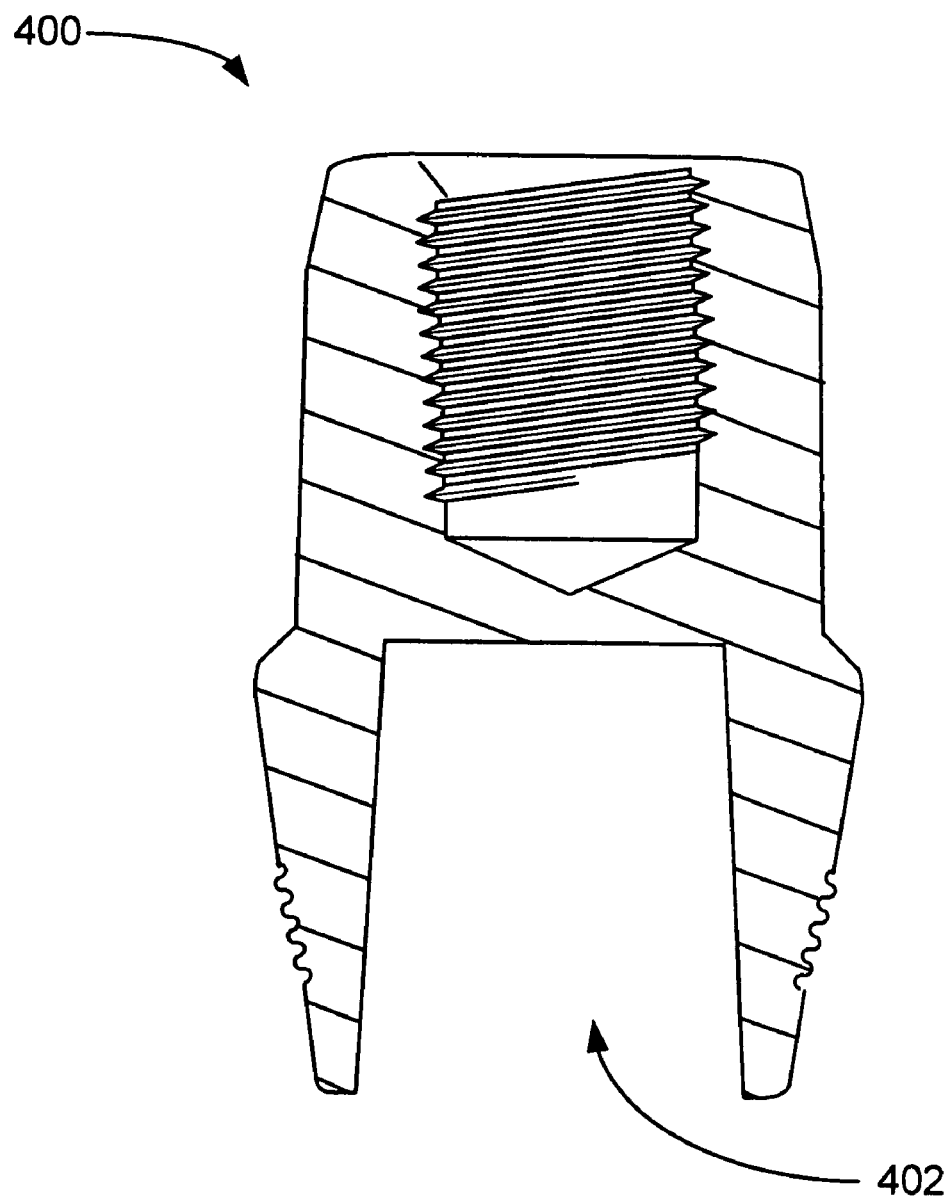

An alternate embodiment of the invention comprises an implant 201 having all of the features of implant 200, with the modification that instead of having an integral abutment, a Morse taper 203 is provided as shown in FIG. 2c, for connecting an abutment to implant 201. FIG. 2c shows the implant 201 in an environment with an exemplary abutment 400 attached. FIG. 4a shows a perspective view of an exemplary abutment 400, and FIG. 4b shows a cross-section of said exemplary abutment 400 having a cavity 402 shaped to accept a Morse taper on the shaft of implant 201.

While a specific embodiment of the invention was chosen for purposes of disclosure, it will be recognized by those of skill in the art that other embodiments of the inventive implant may be provided to meet a specific operating circumstance or bone environment. The invention is, therefore, not considered limited to the specific embodiments chosen. Rather, the invention covers any and all variations of the inventive implant.

As is well known to those of skill in the art, numerous types of abutments may interchangeably be attached to implant 201. Such abutments are believed to be well known and are not further described herein.

Implant 200 has an elongated, substantially cylindrical body 204 having a proximal end 206. Proximal end 206 may protrude from the jawbone, not shown, when implant 200 is installed in a patient's jawbone.

At least one course of helical threads 208 encircles body 204. Threads 208 are typically "knuckle" threads, which, in cross-section, have a quasi-sinusoidal form. In other words, both the crest and root of thread 208 are curvilinear. The crest of threads 208, however, has a pair of helical grooves 212a, 212b formed therein. Grooves 212a, 212b greatly influence the performance of implant 200 when installed in a patient's jawbone against a viscoelastic bone matrix to be osteocompressed. It will be recognized that other numbers of helical grooves or channels may be desirable for a particular bone density and/or application. Therefore, the invention is not limited to a pair of helical grooves. Rather, the invention may have one, two, or more helical grooves.

At least one apical cutting thread 216 is located at the distal end 214 of implant 200. It is preferable to have two cutting threads 216. A cutting thread, preferably the lowermost thread(s), has an edge for cutting through the bone as the implant 200 is installed.

The satisfactory performance of a dental implant depends in large part upon osseointegration (i.e., the growth of bone tissue surrounding the dental implant by the process of osteocompression). Because mechanical implants lack the biological attachment to the bone present in natural dentition, the mechanical design of the implant is of critical importance to reduce stresses and provide functional support and bone stimulation by chewing.

In particular, the implant design must stimulate bone by compression since bone cannot be stimulated by tension as is the case with natural dentition. The areas of an implant's surface capable of providing sufficient bone support and physiologic stimulation are the horizontal compressive planes, not the vertical implant interface under shear force. This fact accounts for failure of many bullet-shaped, push-in implants as evidenced by the Food and Drug Administration's archives of implant failures. Furthermore, if the horizontal planes, or LBAs, of an implant's geometry are not significant enough to sustain the chewing forces generated in a specific bone region, a fibro-osseous condition may ensue. This build-up of connective tissue can cause implant failure under cyclic loading (i.e., chewing). This is particularly prevalent in sharp implants (e.g., blade implants) not having sufficient LBA and typically possessing twice the shear surface area as that of a cylinder or screw implant.

Because the horizontal areas of any implant geometry are the primary mechanism for bone stimulation and implant stability on a long-term basis, any design that increases such horizontal areas can have a significant impact on implant performance. This is especially important in implants that are expected to immediately be functional the day of surgical implantation. The implant 200, specifically the groove structures 212a, 212b, in, the crest 210 provide such enhancement whereby the crestal thread area 210 compresses bone in one direction. Bone responds by immediately compacting bone in the opposite direction into the grooved structures 212a, 212b and the longitudinal channel(s) 213 (described herein below) of the implant of the present invention.

As well as stimulating bone tissue, the LBA 9 load bearing area) of an implant typically sustains and supports approximately 95% of all generated forces imposed on the implant's TSA (total surface area) when the mandible is in centric occlusion. The remaining 5% of force is dissipated throughout the vertical axis of the implant's interface in shear. The enhanced design of threads 208 of implant 200 therefore, also improves the stress handling performance of implant 200.

TABLE 1 shows the LBA and TSA of a variation of the inventive implant, having a shaft, which is 4.0 mm wide.

TABLE 1

| No. of threads | Implant body length (mm) | Approximate LBA of implant 200 (mm$^2$) | Approximate TSA of implant 200 (mm$^2$) |
|---|---|---|---|
| 4.5 | 9 | 93.8 | 179.0 |
| 5.5 | 11 | 107.9 | 207.6 |
| 6.5 | 13 | 121.9 | 236.7 |
| 7.5 | 15 | 136.5 | 266.3 |
| 8.5 | 17 | 151.5 | 295.6 |

The LBA and TSA measurements shown in TABLE 1 for the inventive implant are approximately at least 66% to 75% higher than all known prior art. While specific combinations of shaft width, implant body length, and/or number of threads have been chosen for purposes of disclosure, it will be recognized by those skilled in the art that other shaft width, implant body length, and/or number of threads may be provided to meet a specific operating circumstance or bone environment. The invention is, therefore, not considered limited to the specific shaft width, implant body length, and/or number of threads chosen. Rather, the invention covers any and all variations of shaft width, implant body length, and/or number of threads.

The thread geometry of the novel implant attains high values of implant-to-bone support in a compressive mode at the LBA. Optimum performance of the novel implant is typically obtained by bone compaction of horizontal osseous levels. Such compaction may be maximized using a specialized rotary osteotome, such as that described in co-pending U.S. application Ser. No. 10/668,805, included herein by reference.

Various histologic studies have demonstrated that compression of bone induces extracellular fluids within the bone to flow over the charged surface of osteoblast cells, causing osteogenic activity. In addition, no bone necrosis occurs at the implant's interface due to unique surgical instrumentation and implant congruity at time of implant placement. Due to the unique geometry of the implants of the present invention, controlled functional osteocompression is achieved for a specific bone region by the present implant design, especially when using the aforementioned rotary osteotome.

Immediate implant fixation and stabilization in the bone is further increased by the novel implant thread design. This is accomplished by understanding the elastic modulus and the viscoelastic properties of bone, and matching the two secondary grooves (212a, 212b) for each thread by using at least one rotary osteotome, specifically adapted to the geometry of the implant.

As shown in FIGS. 2a and 2c, it is preferable that least one longitudinal groove or channel 213 is provided along the long axis of the implant 200 facing in a counterclockwise direction to the apical cutting threads for insertion. Henceforth, bone chips do not accumulate unnecessarily at surgical sites by the cutting apical threads and are transferred to the two longitudinal channels to fill such concavities for immediate stabilization and immediate implant fixation in the bone to stop counter-rotation. These longitudinal grooves also prevent over-compression and necrosis of the bone and prevents hydraulic buildup at surgical site to offset edema.

As is believed to be known in the dental implant arts, implants of different lengths, diameters, and thread designs may be required, depending upon the bone ridge width and density of the jaw into which they are placed. Another factor, necessitated particularly by bone condition, is the thread pitch of the implant, selected for various bone qualities and forces delegated in a particular region of the maxilla or mandible.

The nominal structure of a particular implant 200 is dependent upon its intended placement area in the jaw. A force-to-bone-density factor has been established to quantify a ratio between the force expected or generated upon a particular tooth area and the bone density typically found in the bone tissue for supporting the implant after tooth extraction. For example, molar regions in both the maxilla and mandible typically receive biting forces in the range of approximately 100-110 psi. Bicuspid regions typically experience biting forces in the range of 40-50 psi, while central teeth only experience biting forces in the range of approximately 10-30 psi.

There is, however, a known difference in bone density or mineralization between similar portions of the maxilla and mandible resulting in different force-to-bone (FB) regions being defined. FB regions are commonly recognized: FB1-FB3. Since forces come in pairs, Region FB1 is for both upper and lower 12anterior teeth; region FB2 for upper and lower eight bicuspids; and, region FB3 for 12 maxillary and mandibular molars.

TABLE 2 provides information relating length of an implant to its intended implant location.

TABLE 2

| Implant Length | Force-to-Bone Region | Implant Placement Region | Implant Load Bearing Area (mm²) |
|---|---|---|---|
| 9 mm | FB1 | Upper/Lower Anteriors | 57-68 |
| 11 mm | FB2 | Upper/Lower Bicuspids | 69-82 |
| 13 mm | FB3 | Lower Molars | 82-96 |
| 15 mm | FB3 | Upper Molars | 94-110 |

Ironically, the molar regions of greater force magnitude also provide the spongiest bone-to-implant interface. This is region FB3 where bone having the lowest mineral content is located. It should also be noted that significant increase in force magnitude is generated in the molar regions of the jaw having less than desirable bone trabeculation, especially in the maxillary molar region. For instance, the average force on the bicuspid region (FB2) is approximately 100 psi compared to the molar region (FB3) where the average force magnitude is approximately 200 psi in a healthy individual with full dentition. This is because the jaw may be modeled as a class II lever where force magnitude increases in the molar region, and a class III lever from the bicuspids to the anterior incisors where the force magnitude decreases. A class III lever occurs when the resisting force (on the implant design against bone) is between the applied force (by the masseter, temporalis, and medial pterygoid muscles) and the point of rotation or fulcrum (condyle). In the case of the human jaw, this phenomenon doubles the forces in the molar regions relative to that in the bicuspid and anterior regions. Even though the muscles fire with equal force, the implant experiences higher values of force due to class II lever.

The requirement to install implants throughout the maxilla and the mandible has necessitated providing several variations of the implant of the present invention. Some examples of such variations are shown in TABLE 3.

TABLE 3

| Implant Thread Description | Major Diameter ("d" 220) | Minor Diameter ("md" 222) | Thread Pitch ("p" 218) |
|---|---|---|---|
| 3.3 Wide Thread Implant | 3.30 mm | 2.50 mm | 2.00 mm |
| 3.3 Narrow Thread Implant | 3.30 mm | 2.50 mm | 1.55 mm |
| 4.0 Wide Thread Implant | 4.00 mm | 2.50 mm | 2.00 mm |
| 4.0 Narrow Thread Implant | 4.00 mm | 2.50 mm | 1.55 mm |
| 5.0 Wide Thread Implant | 5.00 mm | 3.50 mm | 2.00 mm |
| 5.0 Narrow Thread Implant | 5.00 mm | 3.50 mm | 1.55 mm |

While specific combinations of diameter and/or thread pitch have been chosen for purposes of disclosure, it will be recognized by those skilled in the art that other diameters and/or thread pitches may be provided to meet a specific operating circumstance or bone environment. The invention is, therefore, not considered limited to the specific diameters and/or thread pitches chosen. Rather, the invention covers any and all variations of either diameter or thread pitch.

Conversely, a thread design could be developed to accommodate a tooth extraction site having a tapered cone geometry with the present thread design. All tooth extraction sites (whether from incisors, bicuspids, or molars) are not uniform in nature. However, a common denominator they may have is a tapered cone-shaped geometry from the apex, to an uneven elliptical shape toward the crestal ridge. Since bone quality is spongy toward in the apical root area and denser crestally, it may be advantageous to change the thread design of each implant pitch and its minor diameter.

It has been found advantageous to place the implant in the bone in such a way that a portion of the abutment, whether detachable from or integral with the implant, sits below the bone crest. Referring to FIG. 2a, the line referenced by reference no. 224 shows the preferable height of crestal bone on the inventive implant. The upper portion of the abutment protrudes from the soft tissue into the oral cavity. However, the lower portion of the abutment sits within the bone structure in a tapered fashion. Such countersinking in a tapered fashion provides larger support for an area of high load concentration under constant chewing. Henceforth, this abutment area is part of the overall implant mechanical structure of LBA.

The novel geometry of the implant of the present invention allows a novel approach to the installation thereof, shown generally at reference number 300.

First, a dental practitioner evaluates the density of the maxilla or mandible using x-rays, models, and CT scans, block 302. The practitioner identifies overall structure and jaw trajectory with relevant anatomical landmarks, and notes implant sites on the patient's study cast.

Next, the practitioner identifies proposed implant sites, and measures the distance between vital anatomical structures and opposing teeth, block 304. The practitioner thereby ensures that the implant site can accommodate an ideal distance of approximately 7 mm to 9 mm between implant-to-implant centers, including natural tooth preparations. The practitioner determines the optimal locations for implant placement, keeping in mind all anatomical, functional, and aesthetic considerations.

Next, the dental practitioner administers an anesthetic, preferably local, but may be general, block 306.

Following administration of anesthesia, the dental practitioner inserts into the implant site(s), a prefabricated provisional temporary tooth stent, preferably acrylic, having pre-drilled occlusal holes, block 308.

Next, the dental practitioner marks the bone at the proposed implant site, block 310. Marking is accomplished by inserting a drill through the stent until the drill bit makes contact with the bone. The drill is used to put a notch or other type of mark on the bone at the proposed implant site, preferably by drilling about one millimeter into the bone.

Next, an incision is made crestally exposing the implant site(s), block 312. Buccal and lingual mucoperiosteal flaps are elevated. The incision and flap elevation are extended to enable easy access to and control over the implant sites and to permit a good visualization of jaw morphology and vital anatomical sites.

The incision described in block 312, is then carried distally in order to localize the neurovascular bundles exiting from the mental foramina, block 314. In the upper jaw, the foramen is localized and the position of the naso-palatine canal is established.

If the alveolar ridge is too knife-edged or irregular in either the maxilla or mandible, the ridge is reduced with a surgical round bur, rongeur, or osteotome described in co-pending U.S. patent application Ser. No. 10/668,805, until a crestal bone ridge approximately 1.5 mm to 2.5 mm wider than the selected implant diameter is achieved, block 316. Alternatively, bone augmentation procedures may be considered four to six months prior to implant placement.

Next, an implant profile osteotomy is drilled to an appropriate shape and length, block 318. The profile of the osteotomy should be shaped to accommodate the implant's shape. It should be long enough so that the implant fits into the bone snugly, but comfortably.

Next, the thread areas are compacted, preferably to approximately 3.3 mm, block 320, preferably using rotary dilator(s). The compacting step may additionally include threading if necessary. The dilator preferably operates at an approximate speed of 50 rpm using a surgical motor.

If the bone surrounding the osteotomy is too dense, the practitioner should tap dense bone osteotomy, block 322. An example of bone that usually must be tapped is cortical bone because it is very dense, having an elastic modulus of approximately 3 million. Tapping is a procedure whereby a tap is used to extract or cut out bone from the osteotomy. Tapping is not further described herein since it is believed to be a process that is well known to those of skill in the art.

The implant is next installed in the bone, block 324. Denser bone may require the use of one or two additional osteotomes to cut bone three-dimensionally.

Next, the crestal region of the patient's jawbone is grafted with natural or synthetic bone material, block 326. Preferably, a synthetic, bioactive, resorbable graft, such as that known as OsteoGen®, is used, which prevents the downward migration of epithelium. Synthetic bone grafting of the crestal region produces a more intimate contact between the bone and the implant, and provides maximum adaptation of metal to bone in a compressive state.

Next, soft tissue adjacent the implant site(s) is repositioned and sutured together with uninterrupted or continuous sutures to obtain primary closure over the implants, block 328. Primary closure is not further discussed because it is believed to be a term well known to those of skill in the art. It is preferable that to limit the development of any hematoma formation, a gauze pack is placed over the flaps and the patient is asked to maintain it in place with pressure.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A dental implant for insertion in a maxilla or mandible, comprising:
    a) an elongated, substantially cylindrical shaft having a distal and a proximal end; said proximal end for supporting a dental restoration; said shaft having a threaded section for insertion in the maxilla or mandible;
    b) at least one course of external threads helically disposed on the threaded section of said shaft; said threads comprising a crest region defining the implant's maximum diameter in the threaded section, and a substantially smooth inner core region extending between adjacent crest regions defining the implant's minimum diameter in the threaded section; and
    c) at least two grooves helically disposed in said crest region, wherein the implant's diameter at the bottom of said grooves is greater than the implant's diameter in said smooth inner core region and wherein the distance between said at least two grooves is less than the distance between adjacent crest regions.

2. The dental implant as recited in claim 1, further comprising:
    d) at least one longitudinal channel along a long axis of the implant facing in a counterclockwise direction to the threads to prevent counter rotation.

3. The dental implant as recited in claim 1, wherein said at least one course of threads is disposed along said elongated shaft and extends to a point proximate said distal end thereof.

4. The dental implant as recited in claim 1, wherein said crest region of said at least one course of threads comprises a curvilinear surface.

5. The dental implant as recited in claim 4, wherein the smooth inner core region between said adjacent crest regions has a smooth curvilinear surface.

6. The dental implant as recited in claim 1, wherein said at least two grooves helically disposed in said crest region have a curvilinear cross section.

7. The dental implant as recited in claim 1 wherein said proximal end comprises an integral implant neck for receiving a dental prosthesis.

8. The dental implant as recited in claim 1, further comprising:
    d) means for receiving an abutment, said abutment being used for attaching a dental prosthesis to said proximal end of said shaft.

9. The dental implant as recited in claim 8, wherein said means for receiving an abutment comprises a Morse taper adapted to receive and secure the abutment.

10. The dental implant as recited in claim 9, wherein said abutment is a multifunctional abutment.

11. The dental implant as recited in claim 8, further comprising said abutment wherein said abutment is detachable from said implant.

12. The dental implant as recited in claim 1, wherein an internal thread is disposed in said proximal end substantially parallel to a major axis of said elongated shaft, said internal thread is adapted to secure a dental prosthesis directly to said dental implant.

* * * * *